(12) United States Patent
Denis de Senneville et al.

(10) Patent No.: US 11,504,094 B2
(45) Date of Patent: Nov. 22, 2022

(54) APPARATUS AND METHOD FOR CONTRAST-ENHANCED ULTRASOUND IMAGING

(71) Applicants: (INSERM) Institut National de la Santé et de la Recherche Médicale, Paris (FR); Université de Tours, Tours (FR); CENTRE NATIONAL DE LA RECHERCHE SCIENTIFIQUE, Paris (FR); UNIVERSITE DE BORDEAUX, Bordeaux (FR); Institut Polytechnique de Bordeaux (IPB), Talence (FR)

(72) Inventors: Baudouin Denis de Senneville, Talence (FR); Franck Perrotin, Tours (FR); Jean-Michel Escoffre, Tours (FR); Ayache Bouakaz, Tours (FR)

(73) Assignees: (INSERM) INSTITUT NATIONAL DE LA SANTÉ ET DE LA RECHERCHE MÉDICALE, Paris (FR); UNIVERSITÉ DE TOURS, Tours (FR); CENTRE NATIONAL DE LA RECHERCHE SCIENTIFIQUE, Paris (FR); UNIVERSITE DE BORDEAUX, Bordeaux (FR); INSTITUT POLYTECHNIQUE DE BORDEAUX (IPB), Talence (FR)

( * ) Notice: Subject to any disclaimer, the term of this patent is extended or adjusted under 35 U.S.C. 154(b) by 424 days.

(21) Appl. No.: 16/634,837

(22) PCT Filed: Jul. 27, 2018

(86) PCT No.: PCT/EP2018/070383
§ 371 (c)(1),
(2) Date: Jan. 28, 2020

(87) PCT Pub. No.: WO2019/020781
PCT Pub. Date: Jan. 31, 2019

(65) Prior Publication Data
US 2020/0196986 A1    Jun. 25, 2020

(30) Foreign Application Priority Data
Jul. 28, 2017    (EP) .................................... 17183673

(51) Int. Cl.
*A61B 8/08*    (2006.01)
*G06T 7/00*    (2017.01)

(52) U.S. Cl.
CPC ............ *A61B 8/481* (2013.01); *A61B 8/0866* (2013.01); *A61B 8/5276* (2013.01);
(Continued)

(58) Field of Classification Search
CPC ..... A61B 8/481; A61B 8/0866; A61B 8/5276; G06T 7/0016; G06T 2207/10016;
(Continued)

(56) References Cited

U.S. PATENT DOCUMENTS

2008/0049994 A1    2/2008  Rognin et al.
2008/0228080 A1*   9/2008  Arditi ...................... A61B 8/06
                                                        600/458
(Continued)

OTHER PUBLICATIONS

Baudouin Denis et al., "Development of a Fluid Dynamic Model for Quantitative Contrast-Enhanced Ultrasound Imaging", published on Aug. 29, 2017; (Year: 2017).*

(Continued)

*Primary Examiner* — Mekonen T Bekele
(74) *Attorney, Agent, or Firm* — Cantor Colburn LLP (57) ABSTRACT

An apparatus and a method for contrast-enhanced ultrasound (CEUS) including use of a fluid dynamics model for the analysis of dynamic contrast-enhanced ultrasound (DCEUS).

10 Claims, 7 Drawing Sheets

(52) U.S. Cl.
CPC .. *G06T 7/0016* (2013.01); *G06T 2207/10016* (2013.01); *G06T 2207/10132* (2013.01); *G06T 2207/20024* (2013.01); *G06T 2207/30104* (2013.01)

(58) Field of Classification Search
CPC . G06T 2207/10132; G06T 2207/20024; G06T 2207/30104; G01S 7/52039
See application file for complete search history.

(56) References Cited

U.S. PATENT DOCUMENTS

2013/0077843 A1* 3/2013 Bruder ............... A61B 6/4441
382/131
2017/0196539 A1* 7/2017 Gu .................... A61B 8/481

OTHER PUBLICATIONS

A.F.L. Schinkel et al. "Contrast-enhanced ultrasound: clinical applications in patients with atherosclerosis", Int J Cardivasc Imaging, 2016, vol. 32, pp. 35-48.
B. Braden et al. "Diagnostic value and clinical utility of contrast enhanced ultrasound in Intestinal diseases" Digestive and Liver Disease, 2010, vol. 42, pp. 667-674.
C. Bailey "Contrast Enhanced Ultrasound and Elastography Imaging of the Neonatal Brain: A Review", American Society of Neuroimaging, 2017.
C. J. Arthuis et al. "New Insights into uteroplacental perfusion: quantitative analysis using doppler and contrast-enhanced ultrasound imaging", Placenta, 2013, vol. 34, No. 5, pp. 424-431.
F. Tranquart et al. "Perfusion quantification in contrast-enhanced ultrasound (CEUS)-ready for research projects and routine clinical use", Ultraschall Med, 2012, vol. 33, Suppl 1, pp. S31-S38.
I. Pratikakis et al. "Robust multiscale deformable registration of 3d ultrasound images", International Journal of Image and Graphics, 2003, vol. 3, No. 4, pp. 547-565.
Christopher S. Keator et al. "Contrast-enhanced ultrasound reveals real-time spatial changes in vascular perfusion during early implantation in the macaque uterus" Fertil Sferil, 2011, vol. 95, No. 4, pp. 1316-1321 e1-3.
K. S. Mehta et al. "Vascular applications of contrast-enhanced ultrasound imaging", Society for Vascular Surgery, 2017, vol. 66, No. 1, pp. 266-274.
M. Kaspar et al. "Assessment of microcirculation by contrast-ehanced ultrasound: a new approach in vascular medicine" Swiss Medical Weekly, 2015, vol. 145:w14047.
V. Rafailidis et al. "Contrast-enhanced ultrasound of the carotid system: a review of the current literature", J. Ultrasound, 2017, vol. 20, pp. 97-109.
Y. Fei et al. "Effectiveness of contrast-enhanced ultrasound for the diagnosis of acute pancreatitis: A systematic review and meta-analysis" Digestive and Liver Disease, 2017, vol. 49, pp. 623-629.
Y. Hu et al. "Ultrasound Microbubble Contrast Agents: Application to Therapy for Peripheral Vascular Disease", 2009, vol. 26, No. 4, pp. 425-434.
International Search Report dated Sep. 17, 2018 re: Application No. PCT/EP2018/070383, pp. 1-4, citing: US 2008/0228080 A1, US 2017/0196539 A1 and US 20080049994 A1.
Written Opinion dated Sep. 17, 2018 re: Application No. PCT/EP2018/070383, pp. 1-6, citing: US 2008/0228080 A1, US 2017/0196539 A1 and US 20080049994 A1.

* cited by examiner

APPARATUS AND METHOD FOR CONTRAST-ENHANCED ULTRASOUND IMAGING

TECHNICAL FIELD

The present disclosure relates to contrast-enhanced ultrasound, also referred to in the abbreviated form as "CEUS".

BACKGROUND

Contrast-enhanced ultrasound is a non-invasive imaging technique that has been used extensively in blood perfusion imaging of various organs. This modality is based on the acoustic detection of gas-filled microbubble contrast agents used as intravascular flow tracers. These contrast agents significantly increase the ultrasound scattering of blood, thus allowing the visualization and the assessment of microcirculation (i.e., blood velocity, blood volume fractions) commonly undetectable by Doppler ultrasound (DUS). The rheology of microbubbles in the microcirculation is similar to that of red blood cells, thus demonstrating the microbubbles do not interfere with hemodynamics and have a good safety profile in both cardiac and abdominal ultrasound applications.

To achieve this objective, computer tools are required for the spatio-temporal and quantitative assessment of organ perfusion. Practically, once the bolus injection of the ultrasound contrast agent is performed, the enhancement in the vascular compartment is screened using contrast-specific ultrasound-imaging sequences. Recent efforts are focused on the quantification of parameters related to this enhancement and on the use of these latter as indicators for several pathological conditions. To this end, the average intensity within a region of interest (ROI) is analyzed as a function of time, in the form of a time-intensity curve (TIC). The wash-in and wash-out of the contrast agent within the ROI are subsequently quantified by calculating amplitude and temporal parameters, such as the peak enhancement (PE), the wash-in rate (WiR), the time to peak (TTP), the area under the curve during wash-in (WiAUC).

One of the most recent applications in this field is quantitative assessment of placental perfusion. In contrast to other circulatory beds of the systemic circulation where blood traverses from arteries via capillary beds to veins, placental circulation acts as an open system with the spiral arteries opening in a large lake of blood, namely the intervillous space, with little or no impedance to blood flow. That way, using dedicated small animal ultrasound scanner (Vevo®2100) and TIC-based post-processing software (Vevo®CQ), a recent study reported on real-time monitoring of microbubble perfusion in the uteroplacental unit, across the gestation of rats (C. J. Arthuis, A. Novell, J. M. Escoffre, F. Patat, A. Bouakaz, and F. Perrotin, "*New insights into uteroplacental perfusion: quantitative analysis using doppler and contrast-enhanced ultrasound imaging*" Placenta, vol. 34, no. 5, pp. 424-31, 2013; hereinafter referred to as "Arthuis et al. 2013"). The enhancement of ultrasound contrast in the mesometrial triangle and in the maternal spiral arteries was visualized 1 s after intravenous injection of contrast agents. These agents were then detected through the maternal vessel in the centre of the placenta to the chorionic plate. The perfusion of these agents slowly expanded in the placenta to the basal plate. During the gestation of rats, the blood flow increased from days 14 to 20 in the mesometrial triangle and the placenta. In other recent studies, the CEUS of uteroplacental perfusion in nonhuman primates were conducted using clinical scanners (e.g., Sequoia Systems) and custom-designed CEUS analysis program or image post-processing software were provided by the manufacturers (VueBox®, Bracco, Milan, Italy). Keator et al. reported that CEUS was able to detect the primary placental disc and underlying vessels two days earlier than DUS identified endometrial thickening (C. S. Keator, J. R. Lindner, J. T. Belcik, C. V. Bishop, and O. D. Slayden, "*Contrast-enhanced ultrasound reveals real-time spatial changes in vascular perfusion during early implantation in the macaque uterus*" Fertil Steril, vol. 95, no. 4, pp. 1316-21 e1-3, 2011). Using CEUS, spatial differences in vascular perfusion between the endometrium, myometrium and endometrial-myometrial zone were observed and quantified. Thus, myometrium displayed a higher blood flow than that detected endometrium and junctional zone.

However, using the TIC-based approach, the quantification is typically hampered by two main reasons: first, the exact relationship between the acquired ultrasound-signal and the local microbubbles concentration is hardly achievable. Second, the quantification intrinsically solely relies on temporal intensity variations, the explicit spatial transport of the contrast agent being left out.

BRIEF SUMMARY

The disclosure provides an apparatus and a method for contrast-enhanced ultrasound imaging without the drawbacks associated with the prior art.

In that respect, the present disclosure relates to an apparatus for contrast-enhanced ultrasound imaging, comprising:
- injection means for injecting a contrast agent within a region of interest,
- an ultrasound system for propagating ultrasound waves within said region of interest and detecting ultrasound waves backscattered within said region of interest,
- imaging means for producing a temporal succession of images according to said backscattered ultrasound waves, each image being representative of a spatial configuration of said contrast agent within said region of interest.

The contrast agent may preferably comprise gas microbubbles, preferably inert gas microbubbles.

In a non-limitative example, the region of interest may be located within an organ such as the placenta.

Said images are preferably B-mode images.

According to the disclosure, this apparatus comprises transport calculating means arranged to determine a spatial transport of the contrast agent from successive images.

According to an aspect of the disclosure, the transport calculating means may comprise numerical resolution means for numerical resolution of the following transport equation:

$$I_t + \vec{V} \cdot \vec{\nabla} I = 0$$

where I is a grey level intensity on said images, $I_t$ is a partial temporal derivative of I between successive images, $\vec{\nabla}$ is a spatial gradient operator, $\vec{\nabla} I$ is the spatial gradient of I, and $\vec{V}$ corresponds to said spatial transport between those successive images.

Practically, $\vec{\nabla} I = (I_x, I_y)$ for 2D images, and $\vec{\nabla} I = (I_x, I_y, I_z)$ for 3D images, $I_{x,y,z}$ being the spatial partial derivatives of I.

The spatial transport calculated with this transport equation remains identical whichever function is used to convert the grey levels of the images. It is therefore not necessary to convert the grey levels of the images.

In this transport equation, the transport is calculated taking simultaneously into account both spatial and temporal dimensions.

According to another aspect of the disclosure, the apparatus may comprise resetting means arranged to compensate relative movements between said ultrasound system and said region of interest.

In an embodiment, said resetting means may be arranged to compensate relative movements between said ultrasound system and said region of interest using a gradient driven descent algorithm maximizing an inter-correlation coefficient between successive images.

According to another aspect of the disclosure, the apparatus may comprise a spatial low-pass filter arranged to filter said images.

Said spatial low-pass filter may preferably be a spatial low-pass Butterworth filter.

Such a spatial low-pass filter allows mitigating the impact of local image structures on the spatial transport determined using said transport equation.

The disclosure also relates to a method for contrast-enhanced ultrasound imaging, this method comprising:
propagating ultrasound waves within a region of interest and detecting ultrasound waves backscattered within said region of interest,
producing a temporal succession of images according to said backscattered ultrasound waves, each image being representative of a spatial configuration of said contrast agent within said region of interest.

According to the disclosure, this method comprises determining a spatial transport of the contrast agent from successive images.

According to an aspect of the disclosure, the step of determining said spatial transport may comprise numerical solving of the following transport equation:

$$I_t + \vec{V} \cdot \vec{\nabla} I = 0$$

where I is a grey level intensity on said images, $I_t$ is a partial temporal derivative of I between successive images, $\vec{\nabla}$ is a spatial gradient operator, $\vec{\nabla} I$ is the spatial gradient of I, and $\vec{V}$ corresponds to said spatial transport between those images.

According to another aspect of the disclosure, the method may comprise compensating relative movements between said ultrasound system and said region of interest using a resetting means.

More specifically, the step of compensating said relative movements may comprise maximizing an inter-correlation coefficient between successive images using a gradient driven descent algorithm.

According to another aspect of the disclosure, the method comprises filtering said images using a spatial low-pass filter.

The disclosure also relates to an image processing tool which implements such a method.

The disclosure also relates to a device for contrast-enhanced ultrasound imaging, this device comprising such an image processing tool.

BRIEF DESCRIPTION OF THE DRAWINGS

The above and others features, details and advantages of the present disclosure will become apparent from the following detailed description and the accompanying drawings in which:

FIGS. 2a to 2d show results obtained from in-vitro experiments:

FIGS. 3a to 3h provide example of microbubble transport estimates from the DCEUS of two rats using the proposed approach, obtained from in-vivo experiments. FIGS. 3a to 3d display results associated to a control rat and FIGS. 3e to 3h display results associated to a ligature rat. FIGS. 3a and 3e display a B-mode image with superimposed the manually drawn mask (dashed line) underlying the placenta. FIGS. 3b and 3f, 3c and 3g, and 3d and 3h display DCEUS images acquired 10 s, 15 s and 20 s after the determined microbubble arrival in the placenta, respectively. The corresponding transport field estimates are superimposed. In these results, $\Delta T$, $\delta t$, $\alpha$ and $f_c$ were fixed to common typical values of 60 s, 3 s, 0.1 and $f_0/16$, respectively;

FIGS. 5a to 5h provide assessment of proposed and TIC-based approaches for the classification of the two rat populations (i.e. control and ligature):

FIGS. 7a and 7b provide an analysis of the impact of the cut-of-frequency $f_c$ of the low-pass spatial image filtering and of the regularization parameter $\alpha$ of the numerical scheme on the overall results:

Identical or similar elements are marked with identical reference signs in all of the figures.

DETAILED DESCRIPTION

The disclosure provides an apparatus and a method for contrast-enhanced ultrasound imaging.

The apparatus comprises injection means for injecting a contrast agent within a region of interest. For example, Definity® microbubbles (Lantheus Medical Imaging, Billerica, Mass.) can be injected within a tissue or an organ such as the placenta.

The apparatus also comprises an ultrasound system. This ultrasound system is arranged for propagating ultrasound waves within said region of interest. This ultrasound system is also arranged for detecting ultrasound waves that are backscattered within said region of interest. In this example, the ultrasound system comprises a MS-250 probe (21 MHz centre frequency, 13-24 MHz bandwidth, 75 μm axial and 165 μm lateral resolutions) and a Vevo®2100 ultrasound scanner (VisualSonics Inc., Toronto, Canada). The ultrasound system allows the method of the disclosure carrying out a step of propagating said ultrasound waves within said region of interest and a step of detecting ultrasound waves backscattered within said region of interest.

The apparatus also comprises imaging means for producing a temporal succession of images according to said backscattered ultrasound waves. Each image is representative of a spatial configuration of said contrast agent within said region of interest. Imaging means allows the method of the disclosure carrying out a step of producing said temporal succession of images according to said backscattered ultrasound waves. Said images are preferably B-mode images.

Basically, in this example, the method of the disclosure takes advantage of:
- simultaneous acquisition of dynamic contrast-enhanced ultrasound, also referred to in the abbreviated form as "DCEUS", and
- B-mode images.

In particular, the instantaneous apparent microbubble bunches transport is estimated using a continuity equation of fluid dynamics applied on each acquired DCEUS image (see below). B-mode images are dedicated to the manual delineation of the imaged tissue and to the estimation of possible periodic, spontaneous or drift displacements of the tissue. The latter may be induced either by physiologic activity (breathing or peristaltic) or by motion of the ultrasound probe.

Figure 1:
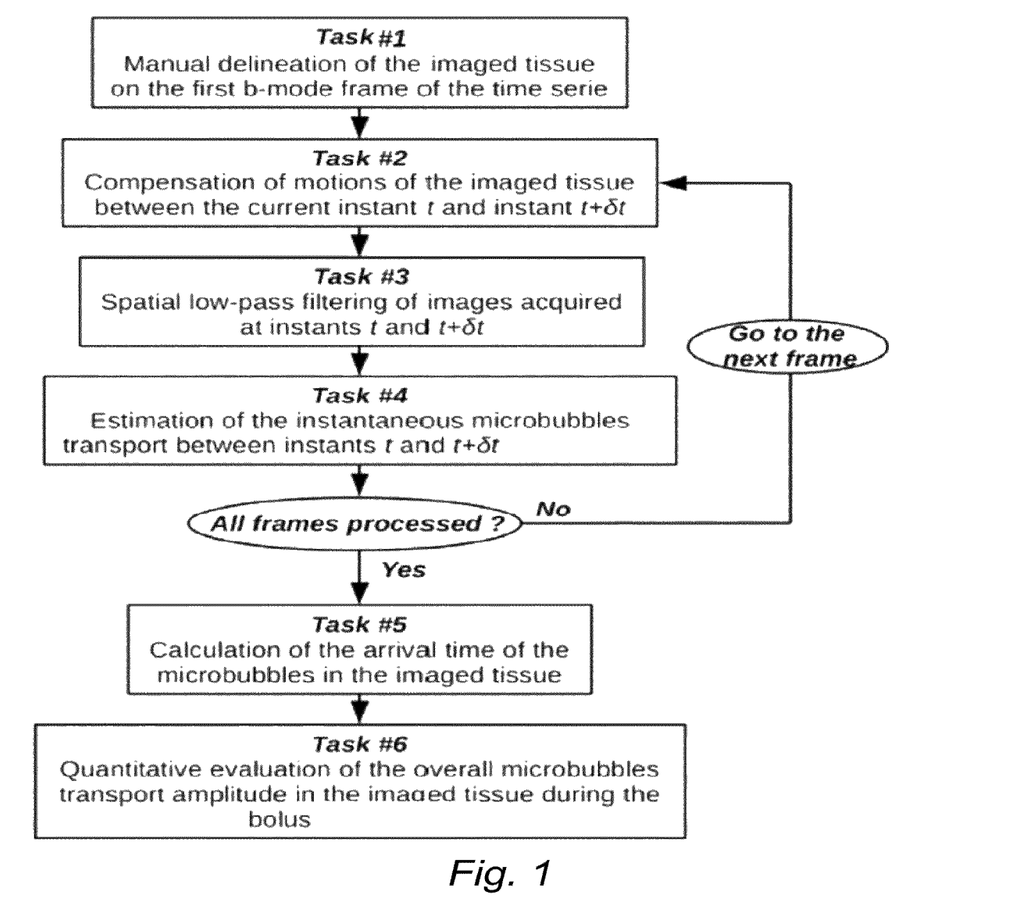
FIG. 1 is a diagram representing different tasks of a method according to the disclosure.

FIG. 1 illustrates one way of carrying out some steps of the method of the disclosure, and describes more specifically six particular steps, or tasks, described below. Those steps or tasks are referred to as "task #1", "task #2" . . . "task #6".

In task #1, said region of interest encompassing the imaged tissue is manually drawn on a B-mode image, and a binary mask (noted Γ) is constructed. Pixels of the image inside the mask have a value of one, and outside a value of zero.

The microbubble transport over the imaged tissue between the current processed DCEUS image (let t be the corresponding acquisition time) and the DCEUS image acquired at t+δt (δt being a pre-defined interval of time) can then be estimated over the successive tasks #2 to #4.

In task #2, physiologic activity and motion of the ultrasound probe are compensated on the DCEUS images, since those relative movements may hamper the estimation of the apparent microbubble transport. In other words, task #2 is intended to compensate relative movements between said ultrasound system and said region of interest.

Using the proposed microbubble transport estimation method, perturbations occur predominantly when the true transport field violates the physical model used for its estimation. Indeed, any temporal change in image intensity is likely to be attributed to microbubble transport. DCEUS image intensity changes can not only be due to contrast change during bolus passage but also to the physiological activity.

In this example, the motion estimation process between t and t+δt is a gradient driven descent algorithm maximizing an inter-correlation coefficient and applied on B-mode images, assuming a translational displacement restricted to the binary mask Γ encompassing the imaged tissue. The estimated spatial transformation is subsequently employed to compensate motions of the imaged tissue on the DCEUS image acquired t+δt.

In task #3, a spatial low-pass filter is applied on each DCEUS image in order to mitigate the impact of local image structures on the employed continuity equation of fluid dynamics.

In this example, a spatial low-pass Butterworth filter (order 1) is applied on DCEUS images acquired at instants t and t+δt in order to mitigate the impact of local image structures on the estimated microbubble transport, due to the differential nature of terms involved in the continuity equation employed afterwards (see below).

In task #4, the instantaneous apparent pixel wise microbubble transport is estimated. The step of the temporal derivative is referred to as δt. The transport between DCEUS images acquired at instants t and t+δt is estimated.

In order to estimate the microbubble bunch transport (noted $\vec{V}$) occurring during the DCEUS between two close instants (i.e. t and t+δt), the following continuity equation can be employed in homogeneous environment: $I_t + \vec{\nabla}.(I\vec{V}) = 0$, where I denotes the grey level intensity on DCEUS images and $I_t$ the partial temporal derivative of I. The left part of this equation is composed by a transient term ($I_t$) and a convection term ($\vec{\nabla}.(I\vec{V})$), which stand for any temporal and spatial grey intensity variations, respectively. The estimated transport field $\vec{V}$ thus accounts for spatio-temporal grey level intensity variations occurring during the dynamic imaging sequence.

In order to associate any spatio-temporal variations of pixel intensities to "transport", without additional assumptions carried on the link between the microbubble dose concentration and grey level intensities, the contribution associated with the divergence of velocity field (i.e. $I\vec{\nabla}.\vec{V}$) is left out. This simplifies the mass continuity equation in the latter equation to the following transport equation:

$$I_t + \vec{V}.\vec{\nabla} I = 0$$

To sum up, the method of the disclosure comprises determining a spatial transport of the contrast agent from successive images. In this example, the step of determining said spatial transport comprises numerical solving of the latter transport equation.

The transport model of the latter transport equation is intrinsically under-determined, and thus leads to an ill-conditioned numerical scheme. The seek transport field $\vec{V}$ can thus be estimated on a pixel-by-pixel basis through the following minimization process:

$$\underset{\vec{V}}{\operatorname{argmin}} \int_{\Omega} |I_t + \vec{V} \cdot \vec{\nabla} I| + \alpha \left( \|\vec{\nabla} u\|_2^2 + \|\vec{\nabla} v\|_2^2 \right) d\vec{r}$$

where $\Omega \subseteq \mathfrak{R}^2$ is the image coordinates domain, (u, v) the estimated pixel wise transport vector components, and $\vec{r} \in \Omega$ the spatial location. The minimized functional accounts for the two following additive contributions:

A data fidelity term (left part of the integral in the latter equation) which optimizes, through a $L^1$ norm, the transport model of said transport equation. Given that a $L^1$ penalizer is employed, transient variations act identically regardless the amount of grey level intensity.

A regularization term (right part of the integral in the latter equation) designed to provide a sufficient conditioning to the numerical scheme. The regularization term is given by $\|\vec{\nabla} u\|_2^2 = u_x^2 + u_y^2$ and $\|\vec{\nabla} v\|_2^2 = v_x^2 + v_y^2$ with $u_x$, $u_y$, $v_x$ and $v_y$ being the partial spatial derivatives of u and v, respectively. Physically, this regularization term assumes that the transport between neighbouring pixels is moderate.

$\alpha$ is a pre-defined weighting factor designed to link these two contributions.

In order to render the latter equation differentiable, $|s| = |I_t + \vec{V} \cdot \vec{\nabla} I|$ can be replaced by $\psi(s) = \sqrt{s^2 + \varepsilon^2}$ with $\varepsilon = 10^{-3}$.

Then, by applying the Euler-Lagrange equations on the latter equation on a pixel-by-pixel basis, one can derive the following system of equations for each $\vec{r} \in \Omega$:

$$\begin{cases} \frac{s}{\psi(s)} I_x - 2\alpha \Delta u = 0 \\ \frac{s}{\psi(s)} I_y - 2\alpha \Delta v = 0 \end{cases}$$

where $I_{x,y}$ denotes the partial spatial derivatives of I, and $\Delta(.)$ the Laplacian operator. Neumann boundaries conditions can be employed.

From here, we have a set of $2*|\Omega|$ non-linear equations with common unknowns u and v.

$\Delta(.)$ can be approximated in the discrete domain with $\Delta u = \bar{u} - u$, $\bar{u}$ being the 3×3 local average of u. That way, two additional implicit linear contributions (along u and v, respectively) are obtained. This approximation allows linearizing the system as follows:

$$\begin{cases} Au + Bv = C \\ Du + Ev = F \end{cases}$$

with $A = I_x^2 + 2\alpha \psi(s)$, $B = I_x I_y$, $C = 2\alpha \psi(s) \bar{u} - I_x I_t$, $D = I_x I_y$, $E = I_y^2 + 2\alpha \psi(s)$, and $F = 2\alpha \psi(s) \bar{v} - I_y I_t$.

Solutions u and v can be found through a fixed-point scheme for which A, B, C, D, E and F are explicitly calculated, as follows:

$$\begin{cases} u^{n+1} = \bar{u}^n - I_x \frac{\bar{u}^n I_x + \bar{v}^n I_y + I_t}{I_x^2 + I_y^2 + 2\alpha \sqrt{(I_t + I_x u^n + I_y v^n)^2 + \varepsilon^2}} \\ v^{n+1} = \bar{v}^n - I_y \frac{\bar{u}^n I_x + \bar{v}^n I_y + I_t}{I_x^2 + I_y^2 + 2\alpha \sqrt{(I_t + I_x u^n + I_y v^n)^2 + \varepsilon^2}} \end{cases}$$

where n+1 denotes a new iteration.

Note that the fixed-point scheme of this latter equation is designed to get the maximum benefit from implicit terms that can be expressed linearly along u and v, while leaving an explicit expression for $\bar{u}$, $\bar{v}$ and $\sqrt{(I_t + I_x u^n + I_y v^n)^2 + \varepsilon^2}$. The residual $\|\vec{V}^{n+1} - \vec{V}^n\|_2$ can be compared to a maximal allowed tolerance of $10^{-3}$ in order to ensure the convergence.

The differential nature of terms involved in said transport equation hampers the estimation of transport of high amplitude. Displacements that are larger than the size of one pixel cannot be estimated. In order to overcome this limitation, it can be adopted a coarse-to-fine strategy as described in the following paper: I. Pratikakis, C. Barillot, P. Hellier, and E. Memin, "*Robust multiscale deformable registration of 3d ultrasound images*" International Journal of Image and Graphics, vol. 3, no. 4, pp. 547-565, 2003). According to this strategy, it can be made iteration of the registration algorithm from a 16-fold down sampled image step by step to the original image resolution.

In addition, an iterative refinement of the transport estimates can be performed within each resolution. This implies running the algorithm several times at the same resolution, initializing the displacement field at the current run of the algorithm with the displacement field that resulted during the previous run. In this manner, the stability of the numerical scheme can be improved and at the same time a better quality of the estimates can be obtained. It is considered that the numerical scheme in the latter equation is converging when the average variation of the transport magnitude from one iteration to the next is smaller than $10^{-3}$ pixels.

In task #5, the instant time of the microbubble arrival is estimated, which for practical reasons is likely to vary from one experiment to the other.

For this purpose, each dynamically acquired image may be iteratively enumerated and the average pixel intensity over the binary mask $\Gamma$ encompassing the imaged tissue can be calculated. Once, this value exceeded a typical pre-defined threshold of 1% of the maximal intensity saturation value, the associated time instant is considered as the arrival time (referred to as $t_0$ throughout the present document).

In task #6, the quantitative microbubble transport amplitude during the bolus can be assessed.

At this stage, a set of pixel wise transport fields is obtained, each one being associated to each ultrasound image. The spatio-temporal averaged microbubble transport (noted $\gamma$), over the imaged tissue and during a time window (covering a duration $\Delta T$, starting from the bolus arrival time $t_0$) can be then calculated as follows:

$$\gamma = \frac{\sum_{t=t_0}^{t_0 + \Delta t} \sum_{\vec{r} \in \Gamma} I(\vec{r}, t) |\vec{V}(\vec{r}, t)|}{\sum_{t=t_0}^{t_0 + \Delta t} \sum_{\vec{r} \in \Gamma} I(\vec{r}, t)}$$

Note that the module of each transport vector $\vec{V}(\vec{r},t)$ is weighted by the amount of grey level intensity in the DCEUS image $I(\vec{r},t)$. That way, similar $\gamma$ values are obtained for scenarios with identical microbubble transports, but various pixel intensities and/or various amounts of pixels exhibiting microbubbles. $\vec{V}(\vec{r},t)$ is converted in mm/s beforehand so as to express $\gamma$ in a common metric unit.

The disclosure also relates to an image processing tool which implements such a method.

The disclosure also relates to a device for contrast-enhanced ultrasound imaging, this device comprising such an image processing tool.

The disclosure also relates to a computer program and/or an image post-processing software comprising instructions for carrying out the method of the disclosure.

Experimental Evaluation

An experimental evaluation was performed using an Intel 2.5 GHz i7 workstation (8 cores) with 32 GB of RAM. The implementation was performed in C++ and parallelized through multi-threading.

Definity® microbubbles (Lantheus Medical Imaging, Billerica, Mass.) were used as ultrasound contrast agent. Definity® microbubbles are a second-generation clinically approved contrast agent, composed of octafluoropropane gas encapsulated in a thin and flexible monolayer of PEGylated phospholipids. The mean diameter ranges from 1.1 to 3.3 μm. Definity® microbubbles were prepared according to the manufacturer's instructions. Briefly, a single vial of Definity® was warmed to room temperature and then was activated using a Capmix® device (3M-ESPE, Cergy-Pontoise, France) for the full 45-second activation cycle.

A high frequency ultrasound scanner was used. More specifically, a MS-250 probe (21 MHz centre frequency, 13-24 MHz bandwidth, 75 μm axial and 165 μm lateral resolutions) connected to the Vevo®2100 ultrasound scanner (VisualSonics Inc., Toronto, Canada) was used to acquire in-vitro and in-vivo images.

Concerning in-vitro experiments, a laboratory-made flow system was an open circuit consisting of 3.59 mm internal diameter flexible silicone tubing, through which a suspension of Definity® microbubbles circulated. The tubing flow system was submerged in a degassed water tank. One end was connected to reservoir filled with degassed water, in which Definity® microbubbles were diluted in physiological serum. The diluted microbubbles solution was subsequently delivered by a peristaltic pump (MCP Process IP65, Cole-Parmer GmbH, Wertheim, Germany). The centre of the flow tube was positioned at a distance of 21 mm from the MS-250 probe. For each experimental condition, a video clip of 30 s was recorded at 20 frames per second (pixel size=0.027×0.027 mm$^2$) using the Vevo®2100 scanner.

After image acquisition, microbubbles perfusion was quantitatively analyzed as follows. The DCEUS-based microbubble transport ($\gamma$) was computed for four regularly sampled flow rates delivered by the peristaltic pump i.e., 1.2, 2.4, 3.6 and 4.8 mL/min). All experiments were independently replicated (N=3). A correlation coefficient (R$^2$) and the $\gamma$-intercept of a linear regression were then calculated in order to assess quantitatively the relationship between the DCEUS-based microbubble transport and the delivered flow rate. The complete evaluation process was repeated for two different microbubble concentrations: 1:1000 and 1:2000 (diluted in physiological serum).

Figure 2:
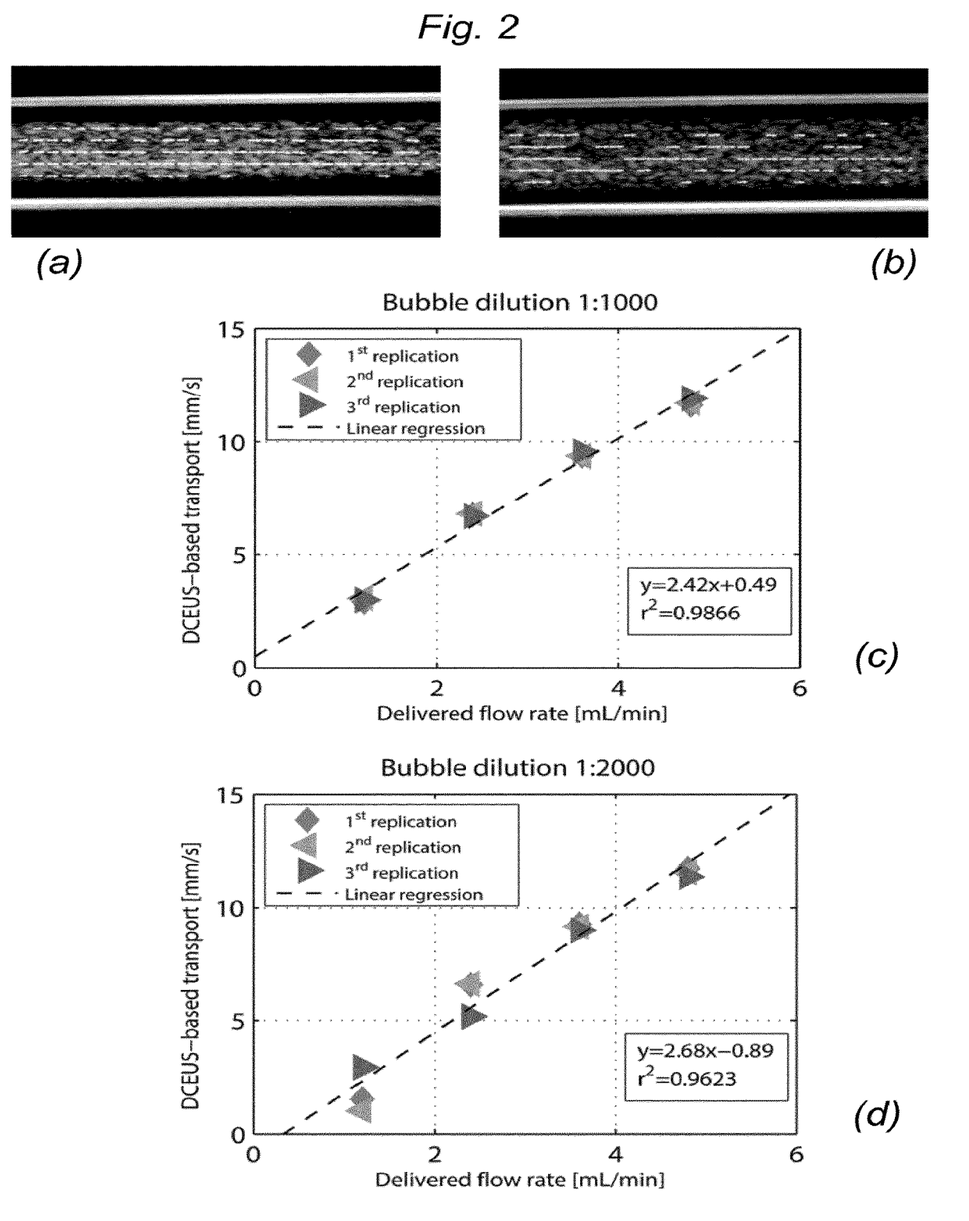
FIGS. 2a and 2b show typical example of DCEUS images of a silicone tubing undergoing a flow rate of 4.8 mL/min with bubble dilutions of 1:1000 (FIG. 2a) and 1:2000 (FIG. 2b)—for an easier visualization, only arrows associated to pixels with DCEUS intensity higher than 10% of the maximal saturation value are displayed.
FIGS. 2c and 2d show DCEUS-based transports flow rate estimates, as a function of the pump flow rate, independently replicated (N=3) for bubble dilutions of 1:1000 (FIG. 2c) and 1:2000 (FIG. 2d). The dashed line represents the linear regression line; its equation and the correlation coefficient are indicated in the text box in the bottom-right of each graph.
Figure 3:
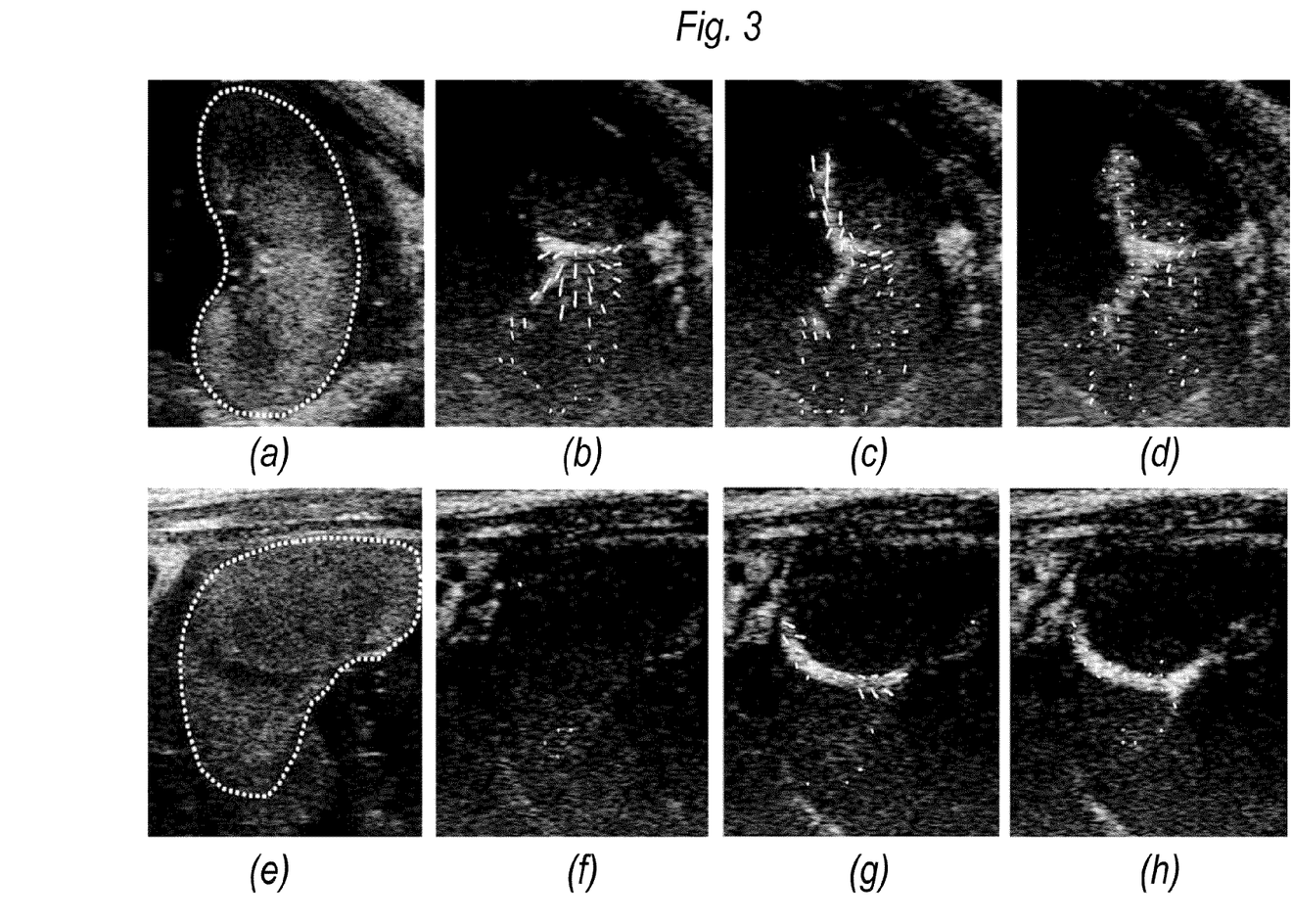

FIGS. 2a to 2d report typical findings obtained using the employed in-vitro experimental platform. A temporal window size $\Delta T=15$ s was employed here. In order to supply as much as possible the high inherent velocity of the microbubble in the silicone tubing, the transport was estimated between consecutive images. In other terms, since the imaging frame-rate was equal to 20 Hz, the temporal derivative step $\delta t$ was set to a value of $\frac{1}{20}$ s. High instabilities of the numerical schemes were observed using the proposed implementation for $\alpha<0.3$. A value of $\alpha=0.3$ was therefore employed to generate the presented results. The cut-of-frequencies $f_c$ of the spatial low-pass filtering of DCEUS images was set to the original image sampling frequency $f_0$ (i.e. no image filtering was applied) in order to mitigate the deterioration of the apparent local shapes of microbubble bunches. FIGS. 2a and 2b display typical examples of DCEUS-based microbubble transport fields (displayed in form of vector fields) estimated using the proposed methodology for microbubble dilutions of 1:1000 (FIG. 2a) and 1:2000 (FIG. 2b). Vectors of homogeneous amplitude and oriented along a common horizontal direction (accurately matching that of the delivered microbubble flow) are observable for each tested bubble dilution. As shown in FIGS. 2c and 2d, the proposed estimated DCEUS-based transport amplitude ($\gamma$) is a good quantitative indicator of the flow rate within the tube, for the two tested bubble concentrations (R$^2>0.96$, y-intercept<1 mm/s). It can be noticed that, for a bubble dilution 1:2000, the precision of $\gamma$ diminished, especially for low delivered flow rates (i.e. 1.2 and 2.4 mL/min). The DCEUS-based microbubble estimation process was in this case impaired by few local image contrasts (see the reduced US contrast within the tube in FIG. 2b, as compared to FIG. 2a), which in turn hampered occasionally the conditioning of the employed numerical scheme.

Concerning in-vivo experiments, all procedures were performed in accordance with the ethical guidelines and were approved by the French Committee (n° 19) for Animal Care and Ethics in Animal Experiments (APAFIS #3879-2016020117195710). Eleven pregnant Sprague-Dawley rats were purchased from Janvier Labs CERJ (Le Genest Saint-Isle, France). They were maintained at constant room temperature with 12 h light cycle. The rats were 10-12 weeks old at the beginning of the experiments, weighing in average 377±17 g. A ligature of the uterine pedicle was performed to induce an IUGR on the seventeenth days of gestation. Under gaseous anaesthesia (Aerrane®r, Baxter, Deerfield, Ill.), the pregnant rats were placed on a thermostatically controlled pad in order to maintain body temperature at about 37° C. Before the surgery, an analgesia was achieved by intraperitoneal (i.p.) injection of buprenorphin (0.05 mg/kg; Buprecare®, Axience SAS, Pantin, France). After shaving of the abdomen, a surgeon performed a midline laparotomy incision with sterile precautions. The number of implantation sites was checked in each uterine horn. A 5-0 Ethilon nylon suture (Ethicon, Somerville, N.J.) was placed around the uterine vessels near the lower end of one horn. The non-ligated horn served as a control. The abdominal incision was repaired in layers using standard surgical procedures. Five hours later, a single 5-mg/kg buprenorphine was intraperitoneally administered to manage postoperative pain.

Under gaseous anaesthesia (Aerrane®), the pregnant rats were placed on a thermostatically controlled pad and their abdomens were shaved before CEUS examination on the nineteenth day of gestation. A 24-gauge catheter was placed in a tail vein to inject Definity® contrast microbubbles. Ultrasound B-scans were used to image foetal-placental unit in cross-section. A bolus of 200 μL of contrast agent (0.5 mL/kg) was intravenously injected. Subsequently, a video clip of 150 s was recorded at 10 frames per second (pixel size=0.035×0.035 mm²) to investigate the utero-placenta perfusion.

After image acquisition, utero-placental perfusion was quantitatively analyzed from the DICOM video data using the proposed methodology. The perfusion was also analyzed using the existing TIC-based approach. For this purpose, we used the CEUS analysis software Vevo-CQ™, which is directly integrated in the ultrasound scanner. The four following parameters were extracted from the TIC: PE, WiR, TTP and WiAUC. The following paper provides a complete description of the above mentioned TIC-based parameters: F. Tranquart, L. Mercier, P. Frinking, E. Gaud, and M. Arditi, "*Perfusion quantification in contrast-enhanced ultrasound (CEUS)—ready for research projects and routine clinical use*" Ultraschall Med, vol. 33 Suppl 1, pp. S31-8, 2012. Note that, for both our approach and tested TIC-based methods, the DCEUS analysis was performed on an identical ROI encompassing the imaged tissue (see Task #1 in FIG. 1) in order to clarify the benefits on the final results.

For the two rat populations, all indicators (i.e. the overall microbubble transport amplitude $\gamma$ as well as the four parameters extracted from the TIC) were expressed as medians and interquartile ranges, and were compared by using the unpaired Mann-Whitney U test. The results were considered significant when the p-value was lower than 0.025. In addition, considering each indicator as a classification criterion, the performance of a binary classifier system was also assessed using a "receiver operating characteristic" (ROC) curve. The area under the ROC curve (AUROC) was subsequently computed: while a binary classifier acts like a completely random guess for AUROC=0.5, the best possible prediction method would yield to a value of 1.

Figure 4:
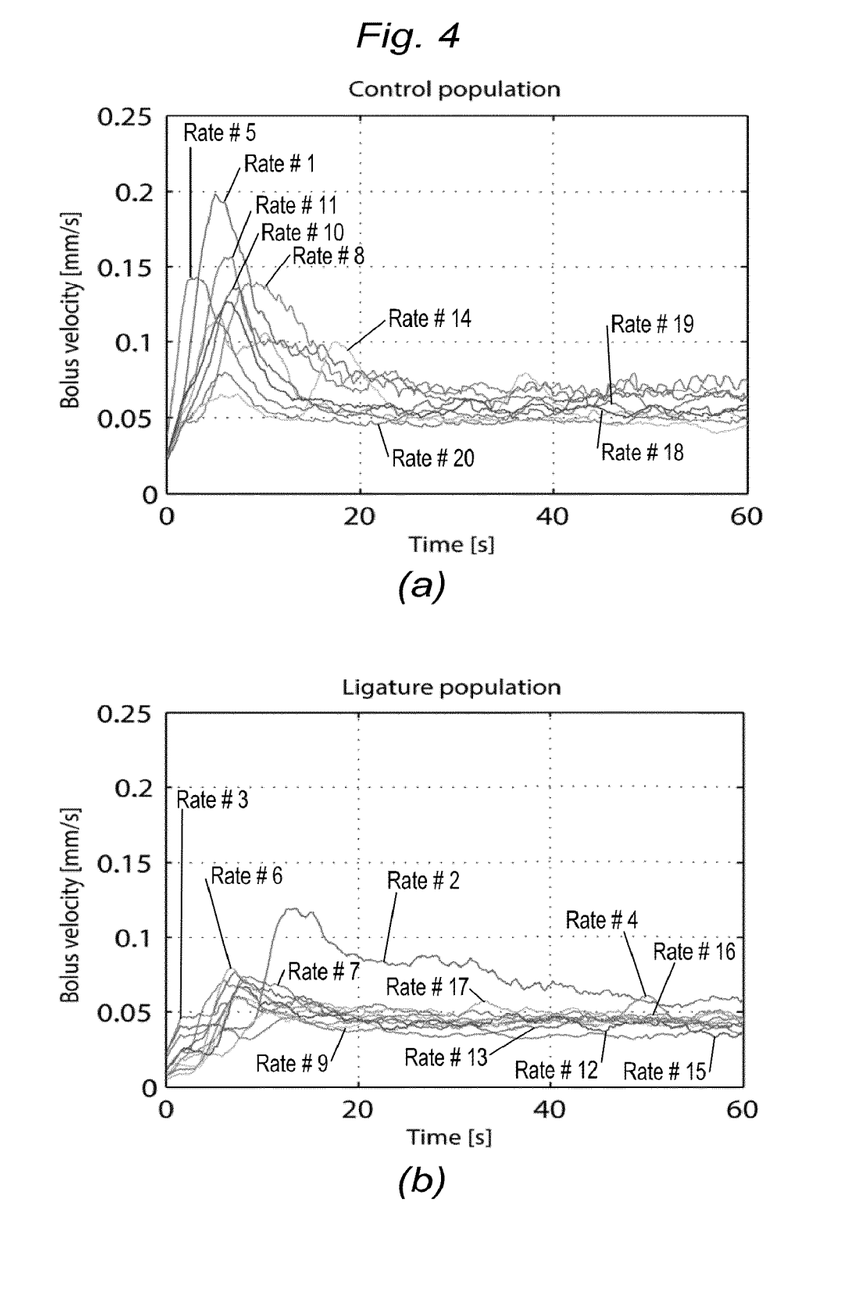
FIGS. 4a and 4b show temporal evolution of the bolus velocity (averaged over the ROI encompassing the placenta, and weighted by the amount of grey level intensity in the DCEUS image) estimated for each control (FIG. 4a) and ligature (FIG. 4b) rat, obtained from in-vivo experiments.
Figure 5:
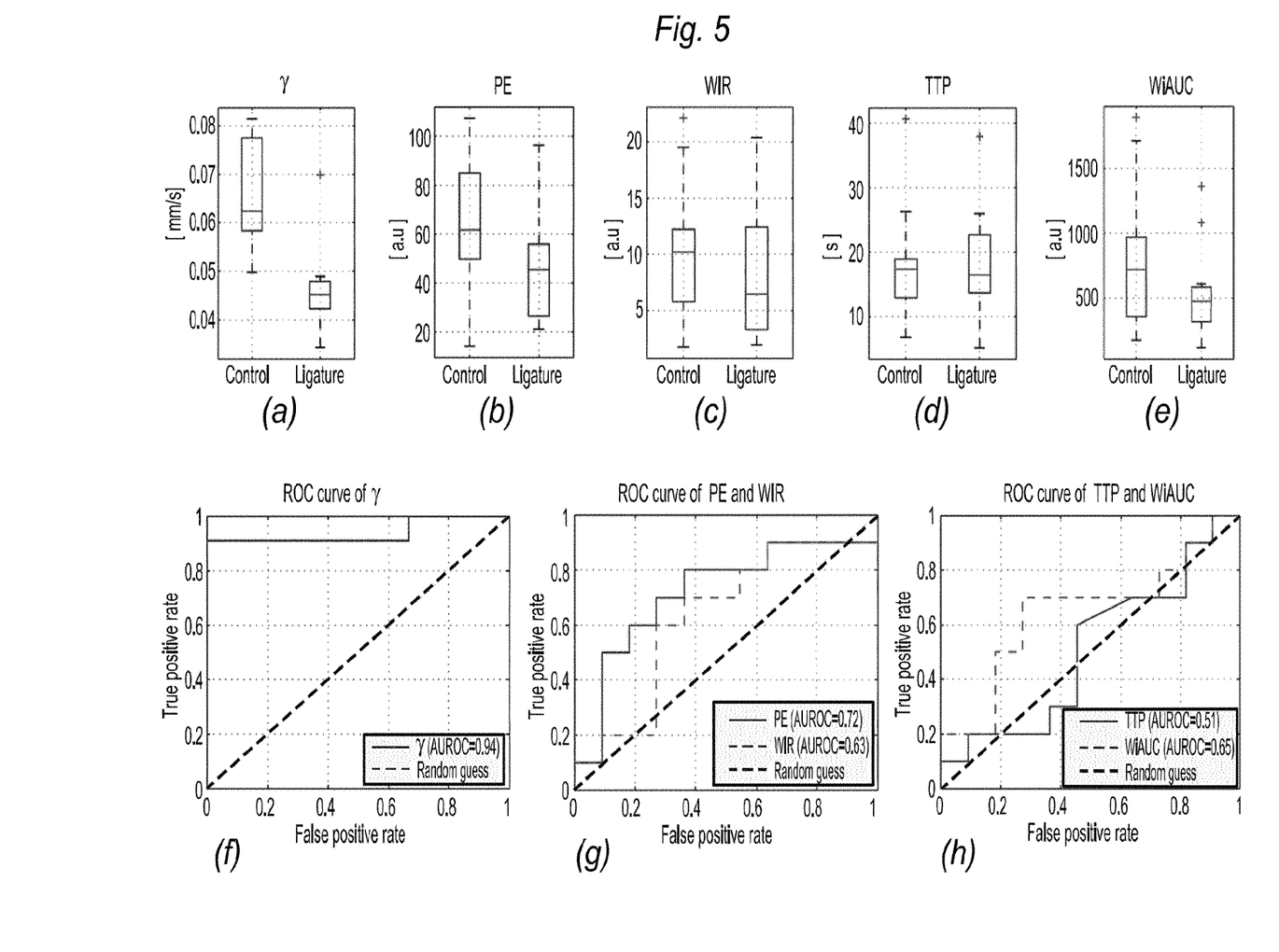
FIG. 5a: boxplots of overall microbubbles velocities estimated over each rat populations using the proposed approach.
FIGS. 5b to 5e: distributions of PE, WiR, TTP and WiAUC estimated over the placenta for the two rat populations using the existing TIC-based approach. Median is shown by the central mark, the first and the third quartile are reported by the edges of the box, the whiskers extend to the most extreme time points which are not considered as outliers, and outliers are individually plotted in red.
FIG. 5f: ROC curve obtained using γ.
FIG. 5g: ROC curves obtained using PE and WiR.
FIG. 5h: ROC curves obtained using TTP and WiAUC.

FIGS. 3a to 3h report typical microbubble transport fields obtained from two dynamic contrast-enhanced experiments (one clip was selected in the control and one in the ligature population, respectively). For each rat, the mask encompassing the placenta, manually drawn in Task #1, is displayed in FIGS. 3a and 3e. The estimated microbubble transports are visually larger for the control population (FIGS. 3b-d) as compared to the ligature population (FIGS. 3f-h) (note that the estimated vector fields follow visually the dynamic contrast-enhancement in associated DCEUS images). This observation is confirmed in FIGS. 4a and 4b: the instantaneous transport of the apparent microbubble was larger for non-ligature rats, especially for images acquired during the first 10 seconds following the bolus arrival in the placenta. The spatio-temporally averaged microbubble transport amplitude (i.e., coefficient $\gamma$) was significantly higher (p-value=$1.1 \times 10^{-3}$) in the control group than in the ligature group (see FIG. 5a). The associated AUROC, displayed in FIG. 5f, was equal to 0.9343. On the other hand, none of tested TIC-based parameters led to a significant difference between control and ligature populations (p-values obtained using PE, WIR, TTP and WiAUC were equal to 0.098, 0.348, 0.972 and 0.285, respectively), as shown in FIGS. 5b to 5e. The best achievable AUROC was obtained using PE (AUROC=0.72), as shown in FIGS. 5g and 5h.

FIGS. 6a and 6b and FIGS. 7a and 7b analyze the sensitivity of the proposed methodology against the four following calibration parameters:

The duration of the observation window $\Delta T$, which determines the time interval after bolus arrival;

The step of the temporal derivative $\delta T$, which determines the time interval for the estimation of the instantaneous microbubble transport;

The cut-of-frequency $f_c$ of the low-pass filter applied on the input DCEUS images. In the present document $f_c$ is expressed as a fraction of the original image sampling frequency $f_0$;

The regularization of the transport equation $\alpha$, which infers the stability of the numerical scheme.

Figure 6:
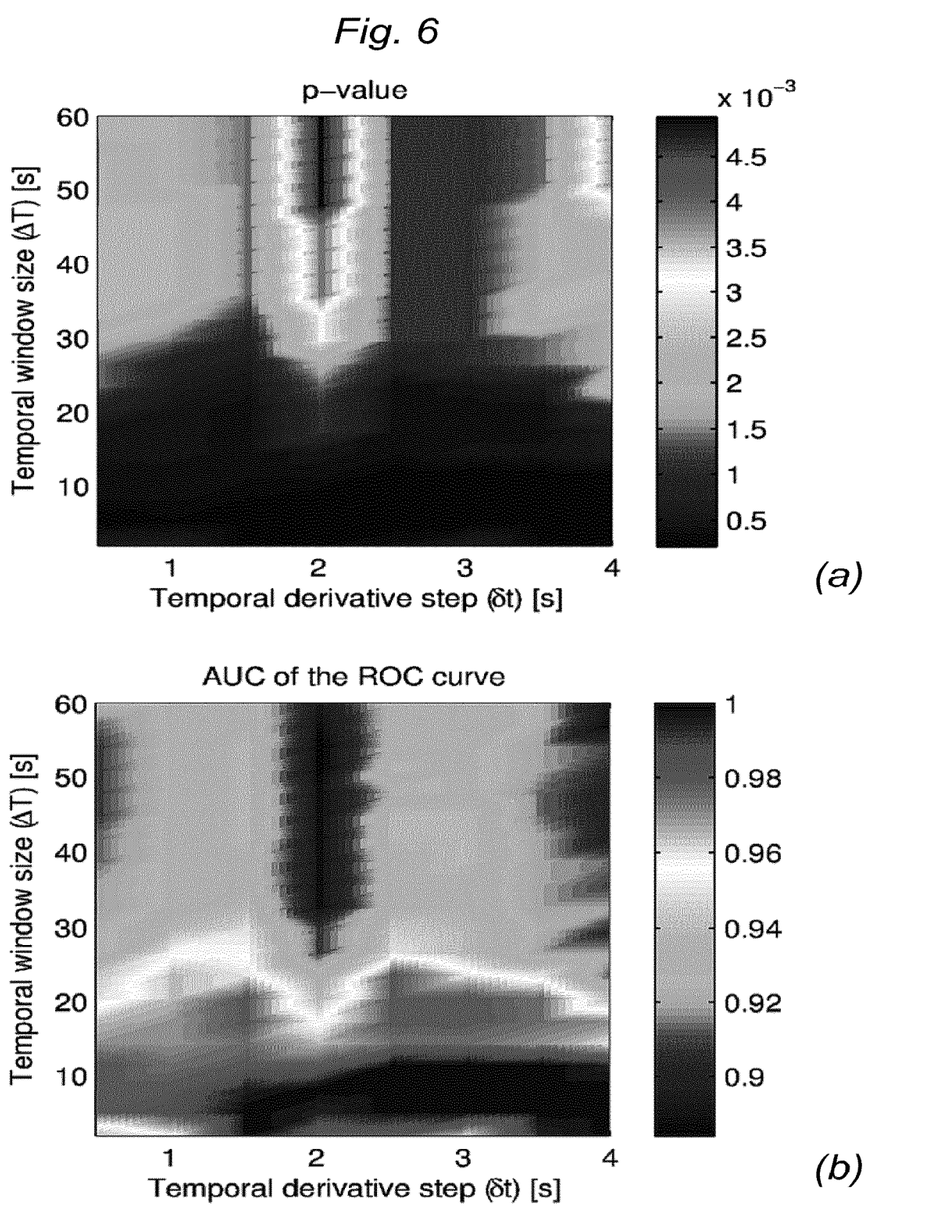
FIGS. 6a and 6b provide an analysis of the impact of the temporal window size ($\Delta T$) and temporal derivative step ($\delta T$) on the overall results obtained in experiments. The bolus velocity was estimated for various values of $\Delta T$ and $\delta T$ ($\alpha$ and $f_c$ being fixed to typical values of 0.1 and $f_0/16$, respectively). The significance of the difference between bolus velocities obtained for the two rat populations (i.e. ligature and control) is reported using the p-value of an unpaired Mann-Whitney U test (FIG. 6a) and the AUROC (FIG. 6b)
Figure 7:
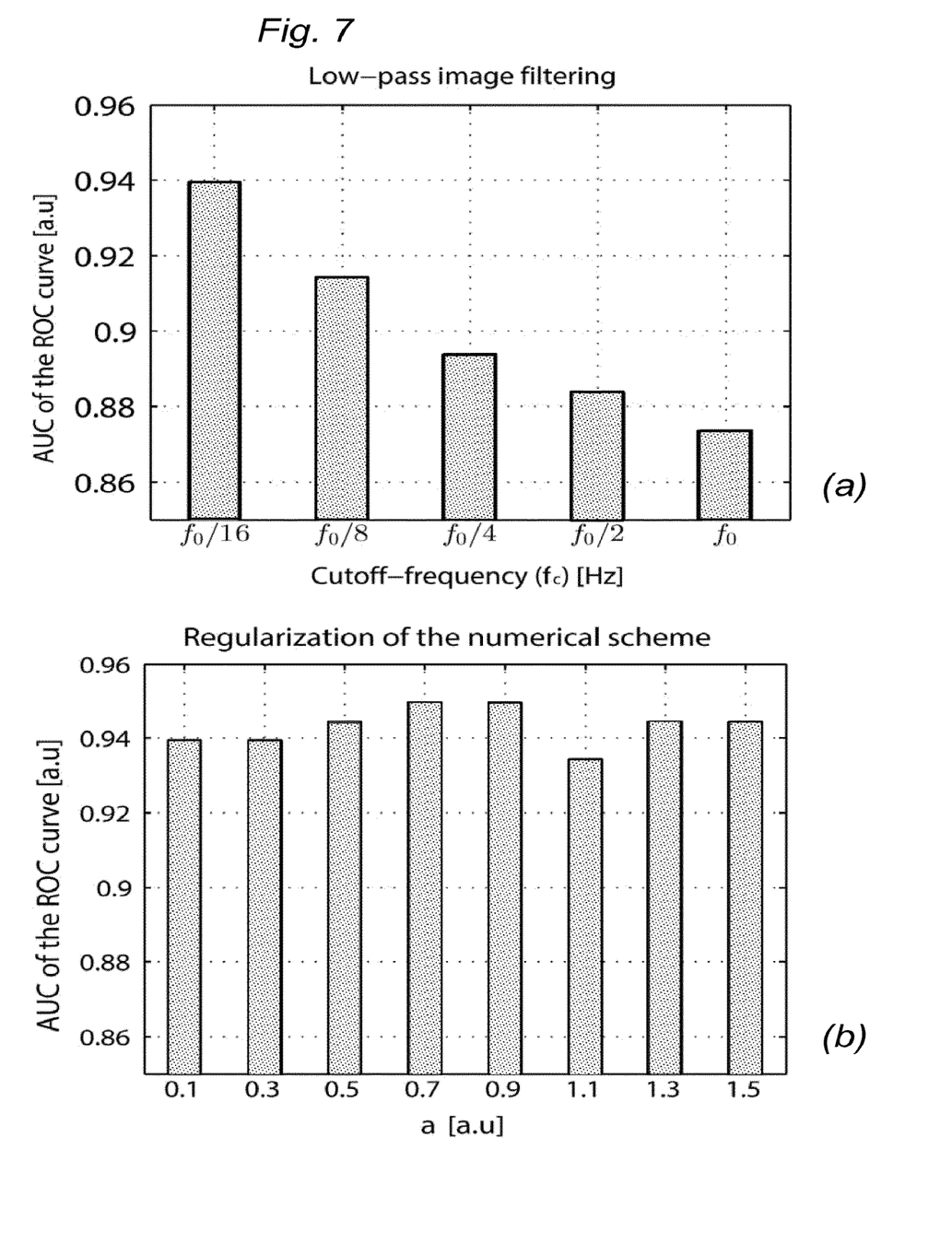
FIG. 7a: bolus velocities estimated for various values of $f_c$ ($\Delta T$ and $\delta T$ and $\alpha$ and being fixed to typical values of 60 s, 3 s and 0.1, respectively)
FIG. 7b: bolus velocities estimated for various values of $\alpha$ ($\Delta T$, $\delta T$ and $f_c$ and being fixed to typical values of 60 s, 3 s and $f_0/16$, respectively). The significance of the difference between bolus velocities obtained for the two rat populations (i.e., ligature and control) is reported using the AUROC.

It can be observed in FIGS. 6a and 6b that $\gamma$ (i.e., the overall microbubble transport amplitude) is a good classification criterion of the two rat populations for all tested temporal window size ($\Delta T$) and temporal derivative step ($\delta t$) (p-value constantly $<10^{-2}$, AUROC>0.89), especially for low values of $\Delta T$ (i.e., <20 s). FIG. 7a shows that the performance of $\gamma$ as a classification criterion for the two rat populations improved when reduced cut-of-frequencies $f_c$ were employed in the spatial low-pass filtering of DCEUS images. This justifies the choice to set $f_c=f_0/16$ in the previously shown results. In addition, it is important to report that high instabilities of the numerical schemes were observed for $\alpha<0.1$. This justifies the choice to set a value of 0.1 as a default parameter for $\alpha$ in the scope of this experiment. FIG. 7b shows that comparable classification performances were assessed for an $\alpha$ value fifteen times higher.

It appears from this experimental evaluation that the estimated transport is highly correlated with the microbubble velocity within our in-vitro system, for the delivered flow rates, whatever the tested microbubble concentration (see FIGS. 2c and 2d). Moreover, the proposed classification criterion $\gamma$, estimated from DCEUS echography, was demonstrated to be a good binary classification criterion for ligature/non-ligature rat placentas. In particular, it outperformed TIC-based methods which provided best results using the parameter PE (AUROC=0.72, as shown in FIGS. 5g and 5h), but remained however well below our fluid dynamic approach (see FIG. 5f).

Conceptually, the proposed fluid dynamic approach analyses pixel wise microbubble velocity fields (both spatial and temporal derivative of the DCEUS image intensity are simultaneously involved in said transport equation). While existing compartment models or TIC-based approaches intrinsically solely rely on temporal intensity variations (the latter being averaged within a mask encompassing the organ of interest), the method of the disclosure performs a simultaneous spatio-temporal analysis. Consequently, this method provides an additional information for the kinetic analysis of DCEUS (see the quantitative estimates on the delivered flow rate in FIGS. 2c and 2d, which are not accessible when using the TIC-based approach together with a continuous infusion of microbubbles). That being said, while a difficult conversion from grey level intensity to microbubble concentration is a common necessary prerequisite when using the existing TIC-based approach, this task is circumvented here.

This advantage of the proposed methodology is illustrated on the presented in-vitro experiment (see FIGS. 2a-d), for which quantitative indicators of the flow rate could be accurately estimated, whatever tested microbubble concentration. Practically, microbubbles generate a hyper-intense signal, which saturates grey level intensities. The histogram of the DCEUS images within the imaged organ consistently depicts two main peaks: while high values correspond to pixels where microbubbles are present, low values are associated to the others. "Binary" DCEUS images are thus obtained which allows the estimation of a wave front displacement using the proposed methodology, regardless microbubble concentration considerations.

The proposed methodology is sensitive to the four above-mentioned calibration parameters. FIGS. 6a and 6b and FIGS. 7a and 7b demonstrate that a compromise has to be found for each parameter, as follows. First, while the duration of the observation window (ΔT) must be high enough to screen a significant microbubble bolus (around 10 seconds were found to be sufficient), this value must be also reduced in order to diminish potential long-term motion bias (e.g., motion of the ultrasound probe, foetus motion . . . ). Second, while the step of the temporal derivative (δt) must be high enough to observe a significant microbubble transport between instants t and t+δt (several seconds provided good results in the employed experimental setup), this value must also be reduced in order to diminish the potential occurrence of physiological motions between the same instants. Third, while the cut-of-frequency of a low-pass filter applied on the input images ($f_c$) has to be low enough to filter regionalized ultrasound artefacts which may be attributed to "false transport" ($f_c=f_0/16$ provided best results on the presented in-vivo data), this value must also be high enough to prevent removing accurate microbubble information. Finally, the regularization parameter (α) in the optimized functional must be high enough to avoid ill conditioning of the numerical scheme 0.1 with the proposed implementation for the proposed in-vivo protocol), it must also be low enough in order to allow estimating local transports. FIGS. 6a and 6b and FIGS. 7a and 7b demonstrate that the four calibration parameters δt, Δt, α and $f_c$ may be fixed permanently for a specific DCEUS imaging protocol. Consequently, a great advantage of the disclosure is that an intervention of the user is only required for the manual determination of the ROI encompassing the imaged tissue.

Using the proposed approach, it is shown that a moderate imaging session duration is mandatory (<20 seconds after the bolus arrival in the placenta, as shown in FIGS. 6a and 6b). This is a great advantage since it diminishes the potential occurrence of long-term bias, including motion of ultrasound probe, foetus motion, etc . . . .

It must be also underlined that the proposed implementation opens good perspectives toward a real-time diagnostic: the employed variational cost function renders itself compatible with a fast linear numerical scheme, while providing a dense pixel wise transport field. Calculations are consequently low time consuming: on the test platform used for this experimental evaluation, less than 100 ms were mandatory for the complete processing of one single frame. Taking into account that the employed imaging frame-rate was equal to 10 Hz for the in-vivo experiments, the processing of one image could be achieved within the interval of time available between two successive acquisitions. An embedded implementation on an ultrasound scanner system for an immediate diagnostic is thus conceivable using available hardware.

Examples of Applications

The disclosure comprises numerous applications, such as for example the clinical diagnostic of obstetrical disorders, the quantitative analysis of the vascularisation of an organ such as the placenta or a tumour, the assessment of vascularisation in abnormal placental perfusion or the assessment of therapeutic efficacy.

Non-limitative examples of applications are described in the following documents:

Arthuis et al. 2013.

C. Bailey, T. A. G. M. Huisman, R. M. de Jong, and M. Hwang, "*Contrast-Enhanced Ultrasound and Elastography Imaging of the Neonatal Brain: A Review*" American Society of Neuroimaging, 2017.

K. S. Mehta, J. J. Lee, A. A. Taha, E. Avgerinos, and R. A. Chaer, "*Vascular applications of contrast-enhanced ultrasound imaging*", Society for Vascular Surgery, vol. 66, no. 1, pp. 266-74, 2017.

A. F. L. Schinkel, M. Kaspar, and D. Staub, "*Contrast-enhanced ultrasound: clinical applications in patients with atherosclerosis*", Int J Cardiovasc Imaging, vol. 32, pp. 35-48, 2016.

Y. Hu, J. Zhu, Y. Jiang, and B. Hu, "*Ultrasound Microbubble Contrast Agents: Application to Therapy for Peripheral Vascular Disease*", vol. 26, no. 4, pp. 425-34, 2009.

M. Kaspar, S. Partovi, M. Aschwanden, S. Imfeld, T. Baldi, H. Uthoff, and D. Staub, "*Assessment of microcirculation by contrast-enhanced ultrasound: a new approach in vascular medicine*", Swiss Medical Weekly, 145:w14047, 2015.

Y. Fei, and W. Li, "*Effectiveness of contrast-enhanced ultrasound for the diagnosis of acute pancreatitis: A systematic review and meta-analysis*", Digestive and Liver Disease, vol. 49, pp. 623-29, 2017.

V. Rafailidis, A. Charitanti, T. Tegos, E. Destanis, and I. Chryssogonidis, "*Contrast-enhanced ultrasound of the carotid system: a review of the current literature*", J Ultrasound, vol. 20, pp. 97-109, 2017.

B. Braden, A. Ignee, M. Hocke, R. M. Palmer, and C. Dietrich, "*Diagnostic value and clinical utility of contrast enhanced ultrasound in intestinal diseases*", Digestive and Liver Disease, vol. 42, pp. 667-74, 2010.

Of course, the disclosure is not limited to the precise embodiments described hereinabove and various adaptations may be effected without departing from the scope of the disclosure as defined in the appended claims. For example, it is to be understood that the present disclosure contemplates that, to the extent possible, one or more features of any embodiment can be combined with one or more features of any other embodiments.

The invention claimed is:

1. An apparatus for contrast-enhanced ultrasound imaging, comprising:
    injection means for injecting a contrast agent within a region of interest,
    an ultrasound system for propagating ultrasound waves within said region of interest and detecting ultrasound waves backscattered within said region of interest,
    imaging means for producing a temporal succession of images according to said backscattered ultrasound waves, each image being representative of a spatial configuration of said contrast agent within said region of interest,
the apparatus further comprises transport calculating means arranged to determine a spatial transport of the contrast agent from successive images, wherein the transport calculating means comprises numerical resolution means for numerical resolution of the following transport equation:

$$I_t + \vec{V} \cdot \vec{\nabla} I = 0$$

where I is a grey level intensity on said images, $I_t$ is a partial temporal derivative of I between successive images, $\vec{\nabla}$ is a spatial gradient operator, $\vec{\nabla} I$ is the spatial gradient of I, and $\vec{V}$ corresponds to said spatial transport between those successive images.

2. The apparatus according to claim 1, comprising resetting means arranged to compensate relative movements between said ultrasound system and said region of interest.

3. The apparatus according to claim 2, in which said resetting means is arranged to compensate relative movements between said ultrasound system and said region of interest using a gradient driven descent algorithm maximizing an inter-correlation coefficient between successive images.

4. The apparatus according to claim 1, comprising a spatial low-pass filter arranged to filter said images.

5. A method for contrast-enhanced ultrasound imaging, comprising:
propagating ultrasound waves within a region of interest and detecting ultrasound waves backscattered within said region of interest,
producing a temporal succession of images according to said backscattered ultrasound waves, each image being representative of a spatial configuration of said contrast agent within said region of interest, and
determining a spatial transport of the contrast agent from successive images, whereby determining said spatial transport comprises numerical solving of the following transport equation:

$$I_t + \vec{V} \cdot \vec{\nabla} I = 0$$

where I is a grey level intensity on said images, $I_t$ is a partial temporal derivative of I between successive images, $\vec{\nabla}$ is a spatial gradient operator, $\vec{\nabla} I$ is the spatial gradient of I, and $\vec{V}$ corresponds to said spatial transport between those images.

6. The method according to claim 5, comprising compensating relative movements between said ultrasound system and said region of interest using a resetting means.

7. The method according to claim 6, in which compensating said relative movements comprises maximizing an inter-correlation coefficient between successive images using a gradient driven descent algorithm.

8. The method according to claim 5, comprising filtering said images using a spatial low-pass filter.

9. An image processing tool, configured to implement a method according to claim 5.

10. A device for contrast-enhanced ultrasound imaging, comprising an image processing tool according to claim 9.

* * * * *